United States Patent [19]

Claremon et al.

[11] Patent Number: 5,152,988

[45] Date of Patent: Oct. 6, 1992

[54] IMIDAZOLE COMPOUNDS IN COMPOSITIONS AND METHODS IN THROMBOLYTIC THERAPY

[75] Inventors: David A. Claremon, Audbon; David C. Remy, North Wales; John J. Baldwin, Gwynedd Valley, all of Pa.

[73] Assignee: Merck & Co., Inc., Rahway, N.J.

[21] Appl. No.: 657,921

[22] Filed: Feb. 20, 1991

Related U.S. Application Data

[62] Division of Ser. No. 476,863, Feb. 7, 1990, Pat. No. 5,019,572.

[51] Int. Cl.$^5$ .................. A61K 37/547; A61K 31/55
[52] U.S. Cl. .................................. 424/94.64; 514/2; 514/161; 514/257; 514/14; 514/213; 514/228.2; 514/255
[58] Field of Search ............ 514/213, 228.2, 255, 514/326, 398, 2, 161, 257, 14; 424/94.63, 94.64

[56] References Cited

U.S. PATENT DOCUMENTS

| | | | |
|---|---|---|---|
| 3,636,003 | 6/1972 | Doebel et al. | 260/309 |
| 3,915,980 | 10/1975 | Gebert et al. | 260/309 |
| 4,460,598 | 7/1984 | Lautenschläger et al. | 424/273 R |
| 4,661,469 | 4/1987 | Sarnoff | 514/2 |
| 5,019,572 | 5/1991 | Claremon et al. | 514/213 |

FOREIGN PATENT DOCUMENTS 0323146  5/1989  European Pat. Off. .

OTHER PUBLICATIONS

Merck Index, 4543 (1983).
Webster, Blood Rev., 1:9–20 (1987) abstract only.

*Primary Examiner*—David M. Naff
*Assistant Examiner*—Sandra Saucier
*Attorney, Agent, or Firm*—Alice O. Robertson; Raymond M. Speer

[57] ABSTRACT

The use of imidazoles of the formula

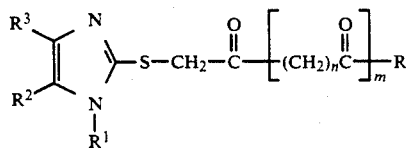

and imidazolium salts of the formula

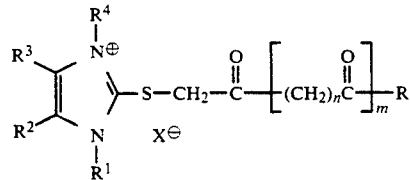

in thromobolytic therapy are described.

7 Claims, No Drawings

IMIDAZOLE COMPOUNDS IN COMPOSITIONS AND METHODS IN THROMBOLYTIC THERAPY

This is a division application Ser. No. 07/476,863, filed Feb. 7, 1990, now U.S. Pat. No. 5,019,572.

BACKGROUND OF THE INVENTION

Transglutaminases, also known as transamidases, are a family of enzymes which catalyze the amide bond formation of the γ-carboxamide group of peptide glutamine residues with an ε amino group of peptide lysine residues.

A number of disease states have been associated with abnormal transglutaminase activity. Thus, for example, in acne lesions, transglutaminase activity in sebaceous follicles has been reported by DeYoung et. al., in J. Investigative Dermatology, 82, 275 (1984). Also, the cornified cell envelope in acne has been reported to be a result of transglutaminase activity by Dalziel et. al., Br. J. Exp. Pathology, 65, 107-115 (1984).

Another dermatological disease, psoriasis, is reported to be associated with excessive transglutaminase activity by Bernard et. al. British Journal of Dermatology, 114, 279 (1986).

Cataracts also have been reported to be associated with elevated transglutaminase activity.

Factor XIIIa is a plasma transglutaminase which is the activated form of Factor XIII also known as fibrinase or fibrin-stabilizing factor. It is essential for normal hemostasis and is responsible for the cross-linking of fibrin.

While the activity of this enzyme may be desirable and essential under most circumstances, activity under certain other circumstances can be highly undesirable. Thus, excessive thrombosis, that is the formation of clot within a blood vessel, gives rise to thrombotic strokes, deep vein thrombosis, variant angina, myocardial infarction, and other medical conditions which frequently result in necrosis of tissues and oftentimes in death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor, plasminogen, and which is activated by plasminogen activators, such as (pro)urokinase, urokinase or tissue plasminogen activator (tPA). Since the occurrence of a thrombotic event calls for rapid remedial action, administration of exogenous tissue plasminogen activator or (pro)urokinase is currently used in thrombolytic or fibrinolytic therapy. However, a still further reduction in lysis time is desirable to minimize cell injury.

Since Factor XIIIa is an enzyme responsible for the final event in the coagulation of blood, lysis and maintaining the lytic state can be facilitated by the presence of a Factor XIIIa inhibitor. Moreover, the presence of a Factor XIIIa inhibitor as in a prophylactic treatment where thrombosis can be anticipated would inhibit hard clot formation. Thus, a Factor XIIIa inhibitor is useful in inhibiting thrombosis, in treating thrombosis when used with a plasminogen activator, platelet aggregation inhibitor, or anticoagulant and in post fibrinolytic therapy in maintaining the lytic state.

STATEMENT OF THE INVENTION

A novel class of imidazole compounds has been discovered which inhibits transglutaminase activity, particularly Factor XIIIa activity. For use as Factor XIIIa inhibitors, the compounds may be used alone or together with agents used in thrombolytic or fibrinolytic therapy such as a plasminogen activator, a platelet aggregation inhibitor or an anticoagulant.

DETAILED DESCRIPTION OF THE INVENTION

The imidazole compounds of the present invention are compounds selected from the group consisting of:

(A) an imidazole represented by the formula

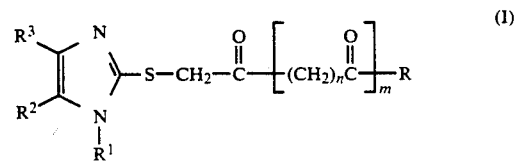

or its acid addition salt, and (B) an imidazolium salt represented by the formula

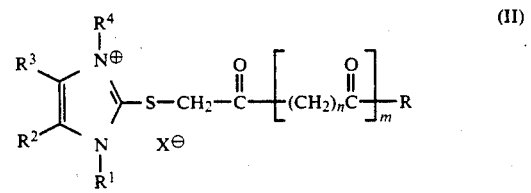

wherein:
R is OR' or NR"R'";
wherein:
R' is hydrogen, lower alkyl, lower alkanoyl, phenyl, or substituted phenyl having from 1 to 3 substituents selected from hydroxy, alkoxy, and nitro and having up to 5 substituents when the substituent is halo;
R" is hydrogen, lower alkyl

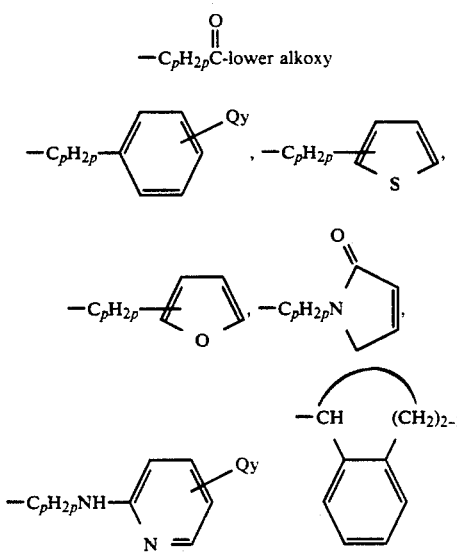

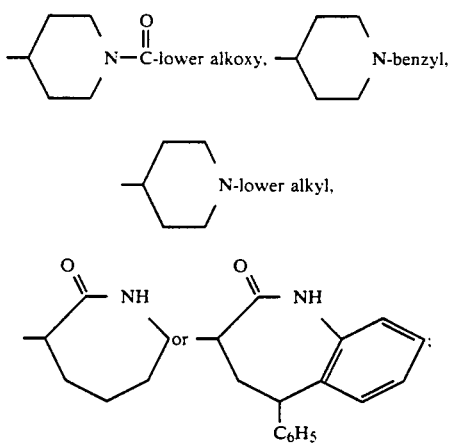

R''' is hydrogen or lower alkyl, or
R'' and R''' together with N is

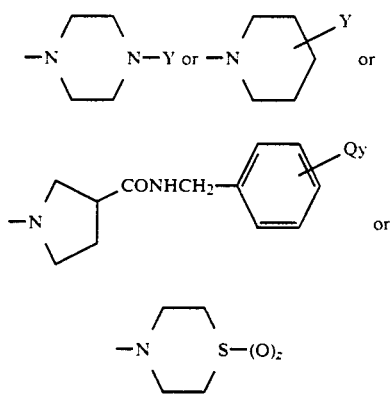

wherein in the foregoing and subsequent formulas, Q is independently hydroxy, lower alkoxy, lower alkyl, halo and nitro Y is lower alkyl,

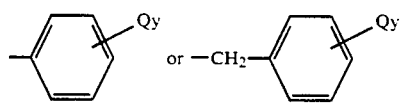

P is 1 to 4,
y is 0 to 4,
z is 0 to 2,
$R^1$ is lower alkyl, benzyl;
$R^2$ is hydrogen, lower alkyl, or cycloalkyl;
$R^3$ is hydrogen, lower alkyl, or cycloalkyl; or
$R^2$ and $R^3$ taken together forms an alkylene chain of 3 to 10 carbon atoms;
$R^4$ is lower alkyl, benzyl;
X is a negative radical of a pharmaceutically acceptable salt;
m is 0 or 1; and
n is from 0 to 3;
provided that when n is 0, m is 0.

By the expressions "lower alkyl" and "lower alkoxy" as employed in the specification and claims are meant branched or straight chain radicals having from 1 to 5 carbon atoms. The expression "cycloalkyl" is meant to embrace 3 to 6 carbon atoms in the ring. The expression "halo" is meant fluoro, chloro, bromo and iodo.

Pharmaceutically acceptable salts suitable as acid addition salts as well as providing the anion of the imidazolium salts are those from acids such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methanesulfonic, ethanesulfonic, trifluoromethanesulfonic and the like, and include other acids related to the pharmaceutically acceptable salts listed in Journal of Pharmaceutical Science, 66, 2 (1977) and incorporated herein by reference.

The compounds, both those which are acid addition salts of the imidazoles and those imidazolium salts represented by formula (II) are generally solids soluble in polar solvents such as methanol, ethanol and the like. The imidazoles of formula (I) are soluble in non-polar solvents such as ethyl acetate, methylene chloride, diethylene chloride, carbon tetrachloride, and the like.

The compounds of the present invention are useful as transglutaminase inhibitors, particularly as Factor XIIIa inhibitors, and are adapted to be employed in thrombolytic therapy. In such use, it is administered to a thrombotic patient or to patients susceptible to thrombotic attack. It is preferably employed together with a plasminogen activator, an enzyme which converts plasminogen to plasmin to increase the rate and extent of lysis. Suitable activators include tissue plasminogen activator (tPA), prourokinase (single chain urokinase), urokinase (dual chain urokinase), streptokinase and eminase (European patent application 028,489). The plasminogen activators may be those isolated from natural sources or produced by recombinant technology and include the genetically engineered variants thereof.

Also, it may be employed together with platelet aggregation inhibitors. Platelet aggregation inhibitors may be drugs, naturally occurring proteins or peptides or may be modified or semi-synthetic proteins or peptides. Established drugs which are platelet aggregation inhibitors include aspirin and dipyridamole. Proteins or polypeptides which are platelet aggregation inhibitors have a certain peptide sequence, most frequently Arg-Gly-Asp. Some classes of natural proteins having this property are fibrinogen receptor antagonists, thromboxane receptor antagonists, thromboxane synthesis inhibitors, collagen receptor antagonists and thrombin inhibitors. Among especially useful polypeptides are those designated "Echistatin" and "Bitistatin" and having the amino acid sequence: X-Cys-R-R-R-Arg-Gly-Asp-R-R-R-R-R-Cys-Y where X is H or an amino acid, Y is OH or an amino acid and each R independently is amino acid, described and claimed in copending applications Ser. No. 184,649, filed Apr. 22, 1988; Ser. No. 303,757, filed Feb. 1, 1989; and Ser. No. 307,642 filed Feb. 7, 1989, all in the names of P. A. Friedman, et. al., the teachings of which are incorporated by reference.

Additionally, the imidazole compounds may be employed for continued therapy after initial relief from thrombotic attack thereby providing a more complete lysis and minimizing complications from reocclusion. Moreover, the imidazole compounds may be employed in post thrombosis therapy together with anticoagulants such as heparin and coumarin drugs.

The preferred compounds for use as transglutaminase inhibitors are the quaternary imidazolium salts.

The compounds to be employed in the practice of the present invention which are imidazoles may be intermediates in the preparation of those compounds which are imidazolium salts.

The imidazoles (I) useful in the present invention may be prepared according to the following equation (1).

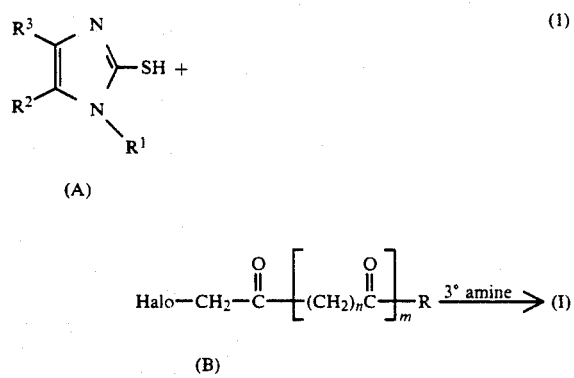

According to this method the 2-mercaptoimidazole (A) starting material, which may be prepared by known procedures hereinafter detailed, is intimately contacted with and caused to react with an acylmethyl halide (B) in the presence of a tertiary amine (3° amine) in an organic solvent at ambient temperature for time sufficient for reaction to take place with the formation of the desired imidazole of formula (I). After completion of the reaction, the imidazole may be recovered from the reaction mixture by removing the solvent by evaporation and purifying the residue by conventional procedures.

Tertiary amines suitable in the reaction include triethylamine, trimethylamine, pyridine, picolines, collidines, and the like.

Suitable solvents of the reaction include acetone, methyl ethyl ketone, dimethylformamide, dimethyl sulfoxide and the like.

In carrying out the reaction, a solution of the acylmethyl halide is added to a solution of the 2-mercaptoimidazole and tertiary amine and the mixture stirred at room temperature for several hours, conveniently overnight. At the end of this period, the solvent is evaporated and the residue partitioned between water and a water-immiscible organic solvent such as ethyl acetate. The organic solution containing the imidazole is washed and dried, the imidazole recovered from the dried solution as residue, and thereafter, purified, preferably by chromatography on silica gel using methanol/chloroform as eluent.

The imidazole then may be employed in the therapeutic method of the present invention as such or as an acid addition salt, or may be treated as an intermediate and employed in the preparation of the imidazolium salts.

The acid addition salts may be prepared in a conventional manner such as by intimately mixing the imidazole and desired acid, preferably in a minimal amount of polar solvent such as ethanol or by other conventional procedures.

The imidazolium salts may be prepared according to the following equation (2)

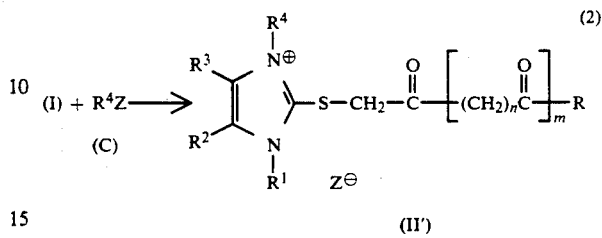

wherein Z is a displaceable group of an active quaternizing agent, and within the definition of X. The reaction is carried out by intimately contacting the reactants in a solvent at ambient temperature for time sufficient for the reaction to take place with the formation of an imidazolium salt (II'). The imidazolium salt (II') may be recovered by conventional procedures and purified, if desired, or converted to another imidazolium salt by use of an anion exchange resin:

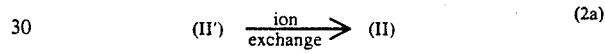

The quaternizing agent is preferably alkyl trifluoromethanesulfonate or other active agent. Thus, the halide and other salts are preferably prepared from the trifluoromethanesulfonate.

The reaction may be carried out for from as little as about two hours to a week, depending on the particular reactants.

In carrying out the reaction, methyl trifluoromethanesulfonate is added to a solution of the appropriate imidazole (I) in a non-polar organic solvent such as methylene chloride and the resulting mixture stirred at ambient temperature for time sufficient for substantial completion of the reaction. At the end of this period, the solvent is vaporized and the residue crystallized to obtain the trifluoromethanesulfonate salt or is converted into a halide or other salt by ion-exchange chromatography, using alkanol/water as solvent. The resulting imidazolium salt is recovered from the eluate and purified, if desired, by conventional procedures.

In a preferred method for the preparation of many of the compounds, an ester derivative is first prepared, i.e., the R group is OR', and the resulting ester is caused to react with an appropriate nitrogen base to obtain the desired compound in which the R group is one in which the hetero atom attached to the carbonyl is nitrogen, i.e., NR"R'". The ester derivative is conveniently one of a strong phenol such as p-nitrophenol or pentachlorophenol. The nitrogen base may be represented by HNR"R'".

The sequence may be seen in the following flow diagram:

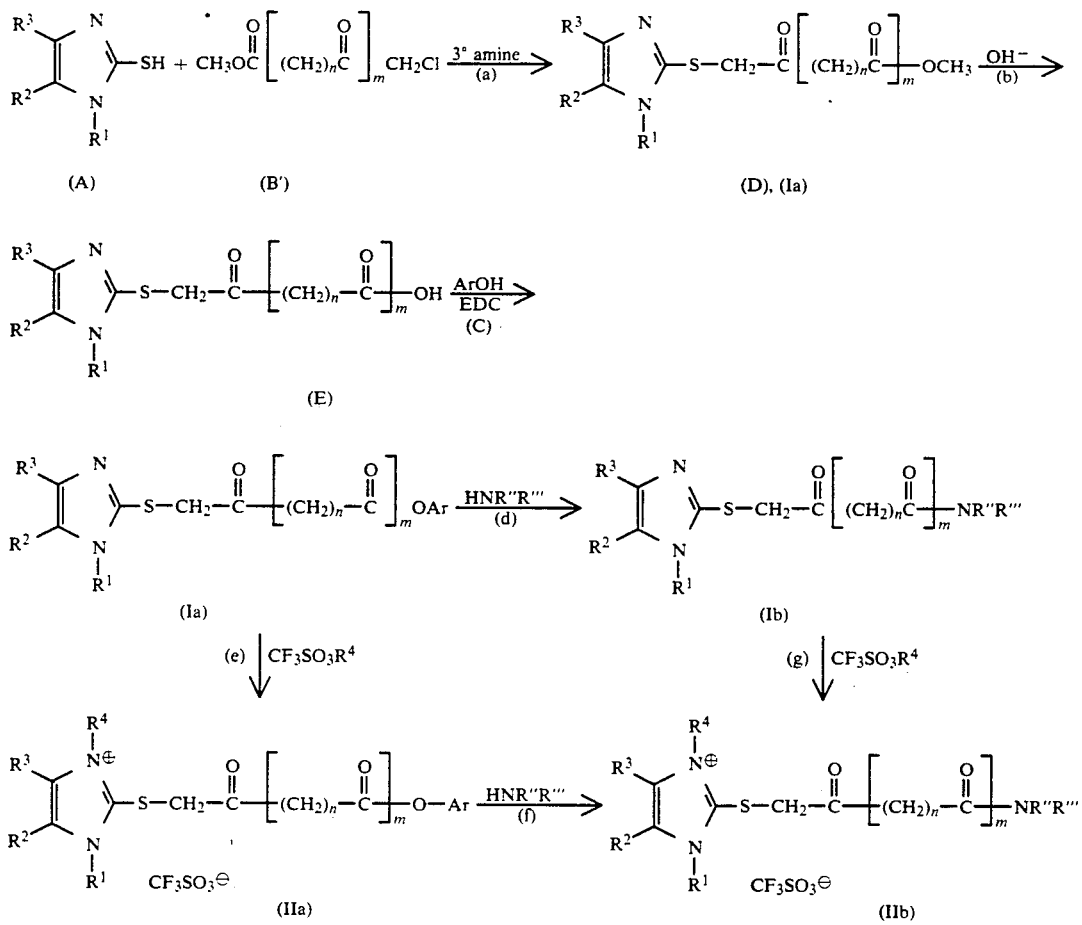

The acyl methyl halide in this method is an ω-carbalkoxyacylmethyl halide (B') which may be prepared by known procedures from a mono-ester-monoacid chloride of a dibasic acid as hereinafter more fully described. This is caused to react with the mercaptoimidazole to obtain an imidazole ester compound (D) which itself may be one of the desired products (Ia where R is OR'). However, it may be also an intermediate for preparing compounds (Ib where R is NR"R''') in which the terminal group is an amide. For this purpose the alkyl ester is converted, preferably, to an aryl (Ar) ester, most preferably to a p-nitrophenyl or pentachlorophenyl ester, and thence by reaction with an appropriate amine base to the desired imidazole Compound Ib.

In the first step of the reaction (step a), the mercaptoimidazole (A) is intimately contacted with the ω-carbalkoxyacylmethyl halide (B') by the dropwise addition of the halide to a solution of the mercaptoimidazole in the presence of a tertiary amine in an organic solvent at ambient temperature for time sufficient for a reaction to take place with the formation of an imidazole ester (compound D) which may be recovered by conventional procedures. Suitable tertiary amines and solvents for this step are previously defined.

Compound D is a compound within the scope of the present invention but also may be an intermediate in the preparation of other compounds within the compounds defined by formula I. It may also be used in the therapeutic method of the present invention as such or as an acid addition salt or employed in the preparation of imidazolium salts (II) using procedures previously described.

In the second step of the reaction (step (b), the methyl (or lower alkyl) ester is hydrolyzed to the acid (Compound E). The hydrolysis may be carried out by intimately contacting the ester (Compound D) with an aqueous alkali metal hydroxide solution. A molar excess of the base is employed. Generally, 10 to 25 percent molar excess is satisfactory. Suitable alkali metal hydroxide are lithium hydroxide, potassium hydroxide and sodium hydroxide. The reaction may be carried out in a water-miscible solvent such as tetrahydrofuran, methanol, ethanol, and the like at ambient temperature for from a few hours to overnight. When the reaction is complete, the reaction mixture is concentrated to remove the solvent, then the residue is diluted with water to dissolve the salt and the aqueous solution extracted with water-immiscible solvent such as ethyl acetate to remove impurities and the remaining aqueous solution acidified. The acid generally does not precipitate from the aqueous mixture so is preferably recovered by continuous extraction for from several hours to overnight. The acid (Compound E) then may be recovered from the solution by vaporizing off the solvent. The acid is within the scope of the invention and may be further purified by conventional methods for therapeutic use, or may be employed in the preparation of imidazolium salts or may be used as an intermediate for the preparation of other imidazole compounds within the scope of the present invention.

When the acid is to be employed as an intermediate for the preparation of other compounds of the present invention, it is converted to an aromatic ester by reaction with an active phenol (ArOH). Particularly useful are substituted phenyl esters such as p-nitrophenyl ester and pentachlorophenyl ester.

The aryl or substituted phenyl ester may be prepared by intimately contacting the acid (compound E) with the appropriate substituted phenol and a dehydrative coupling reagent such as 1-(3-dimethylaminopropyl)ethylcarbodiimide hydrochloride (ECD) according to step (c) in an inert solvent for time sufficient for the reaction to take place with formation of the desired substituted phenyl ester. A slight molar excess of the nitrophenol and the coupling reagent are employed. The reaction is carried out in an inert solvent. Suitable solvents include methylene dichloride, dimethylformamide, tetrahydrofuran and the like.

The reaction is carried out over several hours or overnight. After the reaction is complete, the reaction mixture is diluted with ethyl acetate and the product recovered from the ethyl acetate solution employing conventional procedures.

The aryl (Ia) ester may be employed therapeutically or be converted to the addition salts or to the imidazolium salts.

The imidazolium salts of the esters (IIa, a subclass of II where R is OR') may be prepared in the manner previously described by intimately contacting the ester (Ia) and a quaternizing agent under conditions previously described:

 (3)

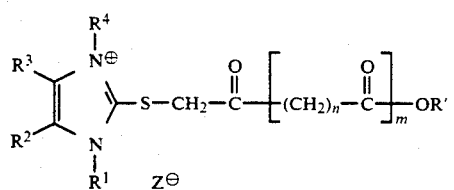

If another salt is desired, the reaction may be carried out on an anion exchange resin as previously described:

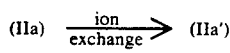 (3a)

The ester may be converted to the amide (Ib; I where R is —NR''R'''). When the amide (Ib) is prepared from the ester (Ia), the ester and an appropriate amine (nitrogen base) are intimately contacted according to step (d) for time sufficient for a reaction to take place with the formation of the desired amide (compound Ib). For the reaction, substantially equimolar amounts of the reactants are employed. The reaction is carried out in a solvent such as ethyl acetate, dimethylformamide, tetrahydrofuran, methylene dischloride. The time for reaction may be a few hours to overnight and ambient temperature is generally employed. After completion of the reaction, the product may be recovered by vaporizing off the solvent under reduced pressure and purified according to conventional procedures.

When it is desired to prepare the imidazolium salt (IIb) of the amide compound (Ib), it is preferable to prepare first the imidazolium trifluoromethanesulfonate salt of an intermediate aryl ester, (IIa), and then convert the ester salt to the desired amide salt (IIb). In such preparation, the ester trifluoromethanesulfonate salt (IIa) is intimately contacted with the appropriate nitrogen base in an inert solvent in accordance with step (f) for time sufficient for a reaction to take place with formation of the imidazolium trifluoromethanesulfonate salt (IIb). Suitable solvents include methylene chloride, chloroform or acetone.

The reaction is carried out at ambient temperature for several hours to overnight. After completion of the reaction, the reaction mixture is concentrated to remove the solvent, diluted with water, and passed through an ion exchange column appropriately charged with the desired anion to obtain an eluant and to recover the desired salt from the eluant by conventional procedures.

Alternatively, the amide is converted directly to the salt in accordance with step (g).

In a similar manner, any imidazolium salt may be converted to another by passing one salt through an anion exchange column previously charged with the appropriate anion for the desired salt.

The usefulness of the compounds as Factor XIIIa inhibitors for enchancing the rate of clot lysis catalyzed by plasminogen activators may be demonstrated first by establishing the inhibitory potencies of the compounds in a Factor XIIIa assay.

The Factor XIIIa inhibitor assay is based on the incorporation of $^{14}C$-putrescine into casein catalyzed by Factor XIIIa. The assay is carried out employing the procedure described in Methods in Enzymology, Vol. 45, Ch 15., pages 177–191 (1976) and using Factor XIII (F XIII) isolated from human plasma. The procedure is summarized briefly and schematically illustrated as follows:

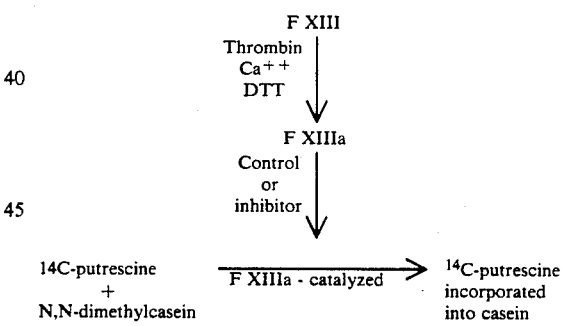

Factor XIII assay mixtures are prepared by adding stepwise, appropriately prepared solutions of thrombin and dithiothreitol (DTT) to a mixture comprising Factor XIII at 140 µg/mL in glycerol/water and tris(hydroxymethyl)aminomethane hydrochloride (Tris·HCl). To a portion of the mixture is added calcium chloride as source of calcium ions required for enzyme activity and to the remaining mixture is added, instead of calcium ions, ethylenediaminetetraacetic acid (EDTA) which serves as a blank for background.

A substrate mixture is prepared from $^{14}C$-putrescine and N,N-dimethylcasein. The assay tubes and control tubes are charged with the substrate mixture and incubated at 37° C. for 20 minutes. Samples are withdrawn from each tube, spotted onto a filter disk which is then immersed in ice cold trichloroacetic acid solution to precipitate the casein on the filter. The filter is then washed to remove unincorporated or free $^{14}C$-putrescine and after drying is counted for $^{14}$C-putrescine incorporated to casein from which percent activity and/or inhibition can be calculated.

Imidazole compounds showing at least 50 percent activity at $2\times10^{-5}$M in the Factor XIIIa assay are considered to be useful in inhibiting hard clot formation, in supplementing fibrinolysis by plasminogen activator, in supplementing the action of a platelet aggregation inhibitor or natural or synthetic anticoagulants. Representative imidazoles and imidazolium salts having IC$_{50}$'s at concentrations below $2\times10^{-5}$M and adaptable to being employed as Factor XIIIa inhibitors are seen in Table I along with properties of most of the various compounds.

TABLE I

| Compd. No. | R | R$^1$ | R$^2$ | R$^3$ | R$^4$ | Anion or Salt | n | M.P. °C. | Mass Spec. M$^-$ |
|---|---|---|---|---|---|---|---|---|---|
| 1 | —OCH$_3$ | —CH$_3$ | H | H | —CH$_3$ | I$^-$ | 3 | 137–138° | — |
| 2 | —NHCH$_2$C$_6$H$_5$ | —CH$_3$ | H | H | —CH$_3$ | Cl$^-$ | 3 | 88–90° | — |
| 3. | —NH—CH(C(=N-2-(N-CH$_3$)C$_6$H$_4$)C$_6$H$_5$)—C(=O)— | —CH$_3$ | H | H | —CH$_3$ | Cl$^-$ | 3 | — | 504 (R) & (S) |
| 4 | —OC$_2$H$_5$ | —CH$_3$ | H | H | —CH$_3$ | Cl$^-$ | 1 | 168–170° | — |
| 5 | —O—C$_6$H$_4$—NO$_2$(p) | —CH$_3$ | H | H | —CH$_3$ | CF$_3$SO$_3^-$ | 3 | 97–99° | — |
| 6 | —NH(CH$_2$)$_2$C$_6$H$_5$ | —CH$_3$ | H | H | —CH$_3$ | Cl$^-$ | 3 | — | 360 |
| 7 | —NH(CH$_2$)$_4$C$_6$H$_5$ | —CH$_3$ | H | H | —CH$_3$ | Cl$^-$ | 3 | — | 374 |
| 8 | —NH(CH$_2$)$_4$C$_6$H$_5$ | —CH$_3$ | H | H | —CH$_3$ | Cl$^-$ | 3 | — | 388 |
| 9. | —NH(CH$_2$)$_3$—N(pyrrolidinone) | —CH$_3$ | H | H | —CH$_3$ | Cl$^-$ | 3 | — | 381 |
| 10. | —NH—(caprolactam) | —CH$_3$ | H | H | —CH$_3$ | | 3 | — | 367 |
| 11 | —OH | —CH$_3$ | H | H | —CH$_3$ | CF$_3$SO$_3^-$ | 3 | — | 257 |
| 12 | —NHCH$_2$-(2-thienyl) | —CH$_3$ | H | H | —CH$_3$ | Cl$^-$ | 3 | — | 352 |
| 13 | —N(piperazinyl)N—C$_6$H$_5$ | —CH$_3$ | H | H | —CH$_3$ | Cl$^-$ | 3 | — | 401 |
| 14 | —NH-(1,2,3,4-tetrahydronaphthyl) | —CH$_3$ | H | H | —CH$_3$ | Cl$^-$ | 3 | — | 386 |
| 15 | —NHCH$_2$-(2-furyl) | —CH$_3$ | H | H | —CH$_3$ | Cl$^-$ | 3 | — | 336 |

TABLE I-continued

| Compd. No. | R | R¹ | R² | R³ | R⁴ | Anion or Salt | n | M.P. °C. | Mass Spec. M⁻ |
|---|---|---|---|---|---|---|---|---|---|
| 16 | —NH—(2-naphthyl) | —CH₃ | H | H | —CH₃ | Cl⁻ | 3 | — | 372 |
| 17 | —N(piperidinyl)—C₆H₅ | —CH₃ | H | H | —CH₃ | Cl⁻ | 3 | — | 400 |
| 18 | —NH—(piperidinyl)N—CO₂C₂H₅ | —CH₃ | H | H | —CH₃ | Cl⁻ | 3 | — | 411 |
| 19 | —N(piperidinyl)—CH₂—C₆H₅ | —CH₃ | H | H | —CH₃ | Cl⁻ | 3 | — | 414 |
| 20 | —NHCH₂CO₂CH₃ | —CH₃ | H | H | —CH₃ | Cl⁻ | 3 | — | 328 |
| 21 | —NH—(piperidinyl)N—CH₂C₆H₅ | —CH₃ | H | H | —CH₃ | Cl⁻ | 3 | — | 429 |
| 22 | —N(piperazinyl)N—CH₂C₆H₅ | —CH₃ | H | H | —CH₃ | Cl⁻ | 3 | — | 415 |
| 23 | —NH—CH₂CH₂NH—(C₆H₄)—NO₂ | —CH₃ | H | H | —CH₃ | Cl⁻ | 3 | — | 421 |

For use in facilitating or supplementing fibrinolytic therapy, the imidazole compound may be administered in a pre- or post-lytic state alone or in combination therapy. Preferably, it is used in a combination therapy with a plasminogen activator, with a platelet aggregation inhibitor, or with a natural or synthetic anticoagulant.

The process for facilitating or supplementing fibrinolytic therapy in prothrombic patients comprises administering a therapeutic dose of an imidazole compound in an amount to provide between 1.4–140 mg/kg/day while considering patient's health, weight, age and other factors which influence drug response. The drug may be administered per os or by injection, and if by injection, either by single injection, multiple injections or continuous infusion.

In the preferred process of the present invention, the imidazole compound is administered with a plasminogen activator in a combination therapy. When combination therapy is employed, it is preferable to administer the Factor XIIIa inhibitor imidazole compound first in a single bolus and thereafter to administer the plasminogen activator by continuous infusion. However, both may be administered simultaneously as a continuous infusate. Under certain circumstances it may be desirable to administer the imidazole compound subsequent to the administration of the plasminogen activator. It is intended that the method of the present invention embrace concurrent administration as well as sequential administration, in any order.

When the Factor XIIIa inhibitor imidazole compound and plasminogen activator are employed in a combination therapy, it is most desirable to use the plasminogen activator in the dose range of about 500 to 10,000 I.U. /kg/minute for from about 30 to 180 minutes and the imidazole compound in the range of 1 $\mu$g-100 $\mu$g/kg/minute for a day (1440 minutes).

When the imidazole compound is to be used with a platelet aggregation inhibitor in combination therapy, the dose range for platelet aggregation inhibitor depends on the nature of the inhibitor. When the platelet aggregation inhibitor is aspirin, the aspirin may be employed at a dose of 25–325 mg once or twice a day. When the platelet aggregation inhibitor compound is dipyridamole, the dipyridamole may be employed at a dose of 25–100 mg four times a day. When the platelet aggregation inhibitor is a semi-synthetic peptide such as "Echistatin" or "Bitistatin", the peptide may be administered in a dose range of 0.1 to 1 nanomole/kg/min. for from 30 to 180 minutes. In each case, the imidazole compound may be employed in the range of 1-100 μg/kg/min. for a day (1440 minutes). The administration may be carried out simultaneously or sequentially in any order as in the procedure for administration with plasminogen activators.

When the imidazole compound is to be used with heparin, heparin may be administered at doses of 4000 to 8000 units per 4 hours and the imidazole compound in the range of 1 μg-100 μg/kg/minute for a day (1440 minutes). When it is to be used with coumarin drugs these drugs are administered orally at doses of 10 to 15 mg/kg/day and the imidazole compound administered by infusion at a rate of 1 μg to 100 μg/kg/minute for a day.

Compositions to be employed in the practice of the present invention whether parenteral, oral or suppository compositions comprises an imidazole compound in a pharmaceutically acceptable carrier.

Parenteral compositions comprise the imidazole compound in sterile physiologically acceptable media such as physiological saline. Such compositions may also contain other ingredients for purposes such as for aiding solubility or for preservation or the like, said ingredients being those acceptable for intravenous administration. The compositions may be prepared as concentrate compositions and lyophilized and then diluted to the appropriate treating composition immediately prior or administration. A therapeutic composition as a unitary dose form may contain from 100 mg to 10 grams of imidazole compound. Compositions suitable in the preferred practice of the present invention of co-administering plasminogen activator and Factor XIIa inhibitor compound may contain about 58 million I.U. of tissue plasminogen activator (tPA) or 1.5 million I.U. of streptokinase and from 100 mg to 10 grams of the imidazole compound.

Oral compositions also may be prepared with the active ingredient in admixture with a pharmaceutically acceptable carrier. Suitable carriers for liquid compositions include water, glycols, oils, alcohols, flavoring agents, preservatives, coloring agents and the like; for solid preparations, starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

Suppository compositions may be prepared by incorporating the imidazole compound into suppository bases such as cocoa butter, polyethylene glycols, polyethylene sorbitan monostearate, ointments, jellies, carbowax and mixtures of these with other compatible materials.

The preparation of the imidazole compounds suitable for inhibiting transglutaminase enzymes, particularly Factor XIIIa, and compositions suitable for carrying out the process of the present invention are illustrated by the following examples but are not to be construed as limiting.

EXAMPLE I

Methyl 7-(1,4,5-trimethylimidazol-2-thio)-6-oxoheptanoate

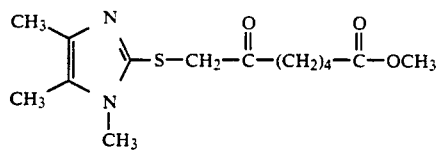

To a suspension of 1.8 grams (0.013 mol) of 4,5-dimethylimidazol-2-thiol and 4.1 milliliter (0.03 mol) of triethylamine in 25 milliliters of acetone cooled to 0° C. was added dropwise a solution of methyl 6-chloro-6-oxo-hexanoate in 20 milliliters of acetone and the resulting mixture stirred overnight at room temperature. At the end of the period, the reaction mixture was concentrated, the residue diluted with ethyl acetate. The ethyl acetate solution was washed successively once with water, once with 5 percent sodium hydroxide solution, twice with water, then once with brine and the washed solution dried over sodium sulfate. The dried solution was concentrated under reduced pressure to obtain 3.2 grams of methyl 7-(1,4,5-trimethylimidazole-2-thio)-6-keto-heptanoate.

EXAMPLE II

6-Oxo-7-(1,4,5-trimethylimidazol-2-thio-)heptanoic acid

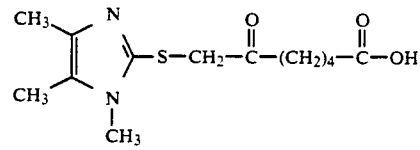

To a solution of 3.1 grams (10.4 mmol) of methyl 7-(1,4,5-trimethylimidazol-2-thio)-6-oxohepanoate (prepared in a manner described in Example I) in 26 milliliters of tetrahydrofuran was added 12.5 milliliter (12.5 mmol) of 1N lithium hydroxide solution and the reaction mixture was stirred at room temperature overnight until it was determined by TLC assay that there was no starting material remaining. The mixture was concentrated to remove the solvent, the residue diluted with water, and the water solution extracted five times with ethyl acetate. The aqueous solution was then acidified to pH 6.5 with 1N hydrochloric acid, sodium chloride added to the aqueous solution and the solution continuously extracted with ethyl acetate over two days to obtain 6-oxo-7-(1,4,5-trimethylimidazol-2-thio)-heptanoic acid in a yield of 2.43 grams.

EXAMPLE III 6-(1,4,5-Trimethylimidazol-2-thio)-5-oxohexanoic acid

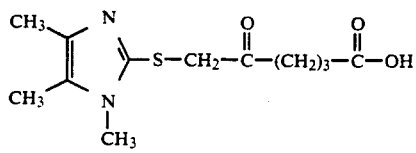

In an operation carried out in a manner similar to that described in Example II, 96 mL of 0.1N sodium hydroxide (9.6 mmol) was added dropwise with stirring to a solution of 1.30 grams (4.6 mmol) of methyl 6-(1,4,5-trimethyl-imidazol-2-thio)-5-oxohexanoate (prepared in a manner described in Example I) in 200 mL of ethanol and the mixture stirred overnight. The ethanol solvent was then removed under reduced pressure and the aqueous solution acidified to pH 6.0 with citric acid. The acidified solution was extracted continuously for 2 days with ethyl acetate and the ethyl acetate extract concentrated to obtain 1.0 gram (81 percent yield) of 6-(1,4,5-trimethylimidazol-2-thio)-5-oxo-hexanoic acid. ¹HNMR (DMSO d6): 1.67 (m,2H), 1.98 (S,3H), 2.06 (S,3H), 2.19 (t,2H), 2.60 (t,2H), 3.42 (S,3H), 3.86 (S,2H).

EXAMPLE IV p-Nitrophenyl-5-oxo-6-[1,4,5-trimethylimidazol-2-thio]-hexanoate

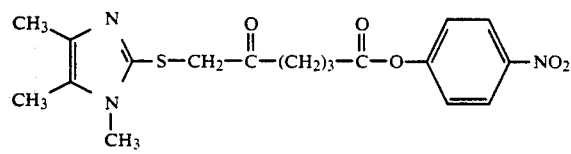

15.5 milliliters of p-nitrophenol (3.7 mmol, 0.51 g), 833 milligrams (3.1 mmol) of 6-[1,4,5-trimethylimidazol-2-thio]-5-oxo-hexanoic acid (prepared as described in Example III) and 0.71 gram (3.7 mmol) of 1-(3-dimethylaminopropyl)-3-ethylcarbodiimide hydrochloride were mixed together in 15.5 milliliters of dry methylene chloride and stirred overnight at room temperature. The reaction mixture was diluted with ethyl acetate and the resulting solution washed successively twice with water, three times with 1N sodium bicarbonate solution, twice with water and once with brine and dried over sodium sulfate. The solvent was vaporized from the dried solution to obtain 1.04 grams of p-nitrophenyl 6-[1,4,5-trimethyl-imidazol-2-yl]thio-5-oxo-hexanoate.

EXAMPLE V 1,2,3,4-Tetramethyl-2-[2,6-dioxo-6-(4-nitrophenyloxy)hexylthio]imidazolium trifluoromethanesulfonate

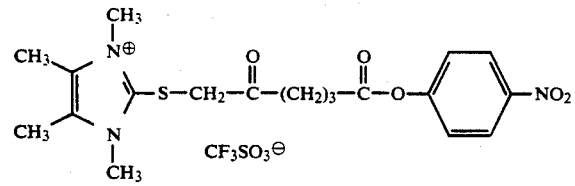

To solution of 1.04 grams (2.6 mmol) of p-nitrophenyl 5-oxo-6-[1,4,5-trimethylimidazol-2-thio]hexanoate, prepared in Example IV, in 15 milliliters of dry methylene chloride, cooled to −15° C. was added 0.3 milliliter (0.43 g, 2.6 mmol) of methyl trifluoromethanesulfonate and the resulting mixture was stirred at room temperature for two hours. Thin layer chromatographic analysis of a sample of the mixture at this time showed the presence of a small amount of starting material. Sixty microliters of methyl trifluoromethanesulfonate was added and the resulting mixture stirred for an additional hour. The mixture was concentrated to dryness under reduced pressure to obtain 1.5 grams of 1,2,3,4-tetramethyl-2-(4-nitrophenyloxy-2,6-dioxohexanylthio)imidazolium trifluoromethanesulfonate.

EXAMPLE VI 1,3-Dimethyl-2-[2,6-dioxo-6-[4-(phenylmethyl)-1-piperazinyl]hexylthio]imidazolium chloride

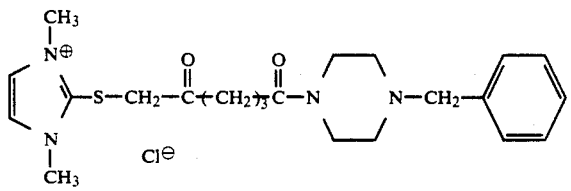

To a solution of 0.2 gram (0.38 mmol) of 1,3-dimethyl-2-[2,6-dioxo-6-(4-nitrophenoxy)hexylthio]imidazolium trifluoromethanesulfonate (prepared in a manner similar to that described in Example V) in 0.8 milliliter of ethyl acetate was added 66 μl (67 mg, 0.38 mmol) of 1-benzylpiperazine and the resulting mixture was stirred at room temperature overnight. The reaction mixture was then concentrated to remove solvent, diluted with water and then made acidic with 1N hydrochloric acid and the aqueous solution passed through an anion exchange resin charged with Cl⁻, the filtrate lyophilized overnight, then triturated with ethyl acetate and stirred at room temperature to obtain the desired 1,3-dimethyl-2-[2,6-dioxo-6-[4-(phenylmethyl)-1-piperazinyl]hexylthio] imidazolium chloride product.

EXAMPLE VII

2-[6-[(2,3-Dihydro-1-methyl-2-oxo-5-phenyl-1H-1,4-benzodiazepine-3-yl)amino]-2,6-dioxohexylthio]-1,3-dimethyl-1H-imidazolium chloride

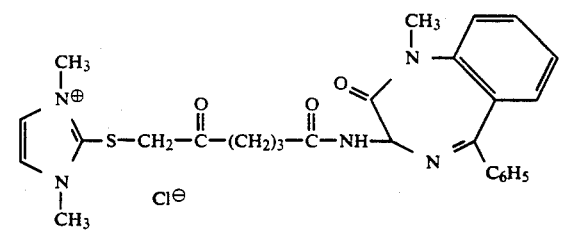

In a operation carried out in a manner similar to that described in Example VI, 0.1 gram (0.38 mmol) of 3-amino-1-methyl-2-oxo-5-phenyl-1H-1,4-benzodiazapine in 0.8 milliliter of dimethylformamide was added to 0.2 gram (0.38 mmol) of 1,3,4,5-tetramethyl-2-[[2,6-dioxo-6-[4-nitrophenyloxy]hexyl]thio]imidazolium trifluoromethanesulfonate and the mixture stirred overnight at room temperature. The mixture was concentrated to dryness. The product was purified by preparative HPLC and then passed through a anion exchange (Cl⁻) column to obtain the above-identified imidazolium chloride.

EXAMPLE VIII 1,3-Dimethyl-2-[2,6-dioxo-6-(2-phenylethylamino)]-hexylthio]imidazolium chloride

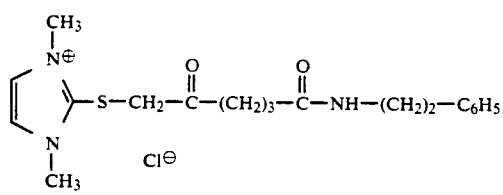

In a similar manner, to 0.2 gram (0.38 mmol) of 1,3-dimethyl-2-[6-(4-nitrophenyloxy)-2,6-dioxohexylthio]imidazolium trifluoromethanesulfonate (prepared in a manner described in Example V) in 0.8 milliliter of ethyl acetate was added 46 µl (g, 0.38 mmol) of 2-phenylethylamine (freshly distilled from CaH$_2$) and the reaction stirred at room temperature. The reaction mixture was then concentrated to dryness and the residue dissolved in water. 46 µl (2 equiv.) of ammonium hydroxide was added and the aqueous solution passed through an ion exchange column charged with Cl$^-$. The chloride product was recovered from the eluate after washing with alcohol and water to obtain the desired 1,3-dimethyl-2-[2,6-dioxo-6-(2-phenylethylamino)]hexylthio]imidazoliumchloride.

EXAMPLE IX

In reactions carried out in a manner similar to that described in the preceding examples, the compounds in Table II are prepared.

TABLE II

| R | R$^1$ | R$^2$ | R$^3$ | R$^4$ | Anion or Salt | n |
|---|---|---|---|---|---|---|
| —OC$_6$H$_5$ | —CH$_3$ | CH$_3$ | CH$_3$ | —CH$_3$ | Cl$^-$ | 3 |
| —OCOCH$_3$ | —C$_3$H$_5$ | H | H | —CH$_3$ | I$^-$ | 2 |
| —OH | —C$_3$H$_5$ | H | H | —C$_2$H$_5$ | CF$_2$SO$_3^-$ | 2 |
| —NH$_2$ | —CH$_2$C$_6$H$_5$ | CH$_3$ | CH$_3$ | —CH$_2$C$_6$H$_5$ | Cl$^-$ | 3 |
| —NH(CH$_3$)$_4$COOCH$_3$ | —CH$_3$ | CH$_3$ | H | —CH$_3$ | I$^-$ | 3 |
| —NH(CH$_3$)$_2$C$_6$H$_5$ | —CH$_3$ | H | H | —CH$_3$ | I$^-$ | 2 |
| —NH(CH$_2$)$_2$-(2-thienyl) | —CH$_3$ | H | H | —CH$_3$ | Cl$^-$ | 2 |
| —NH(CH$_2$)$_3$-(2-oxocyclopentyl) | —CH$_3$ | H | H | —CH$_3$ | Cl$^-$ | 2 |
| —NH-(4-benzylcyclohexyl) | —CH$_3$ | H | H | CH$_3$ | Cl$^-$ | 2 |
| —OC$_6$H$_5$ | —CH$_3$ | H | H | H | — | 3 |
| —OCH$_2$C$_6$H$_5$ | —C$_2$H$_5$ | H | H | H | — | 3 |
| —NH(CH$_2$)$_3$C$_6$H$_5$ | —CH$_3$ | H | H | H | — | 3 |
| —NH(CH$_3$)$_2$NHC$_6$H$_4$NO$_2$(P) | —CH$_3$ | H | H | —CH$_3$ | Cl$^-$ | |
| —N(piperazinyl-N-C(O)OC$_2$H$_5$) | —CH$_3$ | H | H | —CH$_3$ | Cl$^-$ | 3 |
| —NH-(4-benzylpiperazinyl) | —CH$_3$ | H | H | —CH$_3$ | Cl$^-$ | 3 |
| —NH-(4-isopropylpiperazinyl) | —C$_2$H$_5$ | H | H | —C$_2$H$_5$ | Cl$^-$ | 3 |
| —NH-(caprolactamyl) | —CH$_3$ | H | H | —CH$_3$ | Cl$^-$ | 3 |

TABLE II-continued

| R | R¹ | R² | R³ | R⁴ | Anion or Salt | n |
|---|---|---|---|---|---|---|
| −N(−CH₂CH₂−)₂SO₂ (thiomorpholine-1,1-dioxide) | −CH₃ | H | H | −CH₃ | Cl⁻ | 3 |

EXAMPLE X

In reactions carried out in a manner similar to that described in the preceding examples, the compounds in Table III are prepared:

TABLE III

| R | R¹ | R² | R³ | R⁴ | Anion or Salt | n |
|---|---|---|---|---|---|---|
| −NH−(1,2,3,4-tetrahydronaphthyl) | −CH₂C₆H₅ | H | H | −CH₂C₆H₅ | Cl⁻ | 3 |
| −NHCH₂−(2-furyl) | −CH(CH₃)₃ | H | H | −CH(CH₃)₂ | CF₃SO₃⁻ | 3 |
| −N(−piperidine-4-yl)−CH₂C₆H₅ | −(CH₂)₃CH₃ | H | H | −(CH₂)₃CH₃ | CF₃SO₃⁻ | 4 |
| −NHCH₂CO₂CH₃ | −CH₂C₆H₅ | H | H | −CH₂C₆H₅ | Cl⁻ | 4 |
| −NHCH₂CO₂CH₃ | −CH₃ | −C₆H₁₁ | −C₆H₁₁ | CH₃ | CF₃SO₃⁻ | 3 |
| −NHCH₂−(2-thienyl) | −CH₃ | H | H | CH₃ | CF₂SO₃⁻ | — |
| −NHCH₂−(2-thienyl) | −CH₂C₆H₅ | −C₆H₁₁ | −C₆H₁₁ | −CH₂C₆H₅ | CF₂SO₃⁻ | — |
| −NHCH₂−(2-thienyl) | −C₂H₅ | −C₆H₁₁ | H | −C₂H₅ | Cl⁻ | 3 |
| −N(−piperazine)N−C₆H₅ | −CH₃ | H | H | −CH₃ | Cl⁻ | 3 |
| 2-(CONHCH₂C₆H₅)-pyrrolidinyl | −CH₃ | H | H | −CH₃ | Cl⁻ | — |

TABLE III-continued

| R | $R^1$ | $R^2$ | $R^3$ | $R^4$ | Anion or Salt | n |
|---|---|---|---|---|---|---|
| | $-C_2H_5$ | H | H | $-C_2H_5$ | $Cl^-$ | — |
| | $-C_2H_5$ | H | H | $-C_2H_5$ | $Cl^-$ | — |

EXAMPLE XI 1,3-Dimethyl-2-[2,6-dioxo-6-(2-thienylmethylamino)-hexylthio]imidazolium chloride

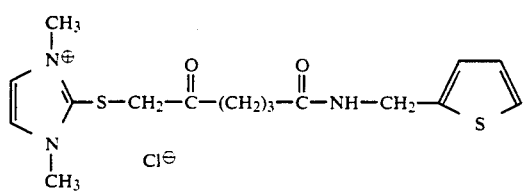

In a similar manner, to 0.2 gram (0.38 mmol) of 1,3-dimethyl-2-[6-(4-nitrophenyloxy)-2,16-dioxohexylthio]imidazolium trifluoromethanesulfonate (prepared in a manner described in Example VI) in 0.8 milliliter of ethyl acetate was added 39 μl 0.38 mmol) of 2-thiophenemethylamine and the reaction stirred at room temperature. The reaction mixture was then concentrated to dryness and the residue dissolved in water. 46 μl (2 equiv.) of ammonium hydroxide was added and the aqueous solution passed through an ion exchange column charged with Cl−. The chloride product was recovered from the eluate after washing with alcohol and water and freeze drying to give the product as a glass.

EXAMPLE XII 1,3-Dimethyl-2-[2,6-dioxo-6-(2-furylmethylaminoamino)hexylthio]imidazoluim chloride

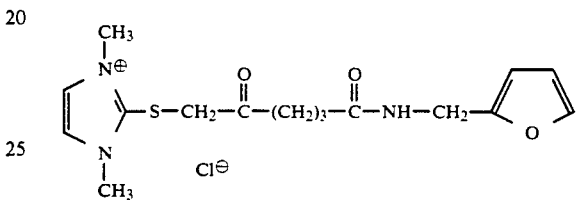

In a similar manner, to 0.2 gram (0.38 mmol) of 1,3-dimethyl-2-[6-(4-nitrophenyloxy)-2,16-dioxohexylthio]imidazolium trifluoromethanesulfonate (prepared in a manner described in Example VI) in 0.8 milliliter of ethyl acetate was added 33.6 μl 0.38 mmol) of furfurylamine and the reaction stirred at room temperature. The reaction mixture was then concentrated to dryness and the residue dissolved in water. 46 μl (2 equiv.) of ammonium hydroxide was added and the aqueous solution passed through an ion exchange column charged with Cl−. The chloride product was recovered from the eluate after washing with alcohol and water to obtain the desired 1,3-dimethyl-2-[2,6-dioxi-6(2-furfurylamino)hexylthio]imidazolium chloride as an oil.

EXAMPLE XIII

In reactions carried out in a manner similar to that described in the preceding examples, the compounds in Table IV may be prepared:

TABLE IV

| R | $R^1$ | $R^2$ | $R^3$ | $R^4$ | Anion or Salt | n |
|---|---|---|---|---|---|---|
| $-NH-CH_2CH_2-\text{C}_6H_4-OH$ | $-C_4H_9(n)$ | H | H | $-C_4H_9(n)$ | $CF_3SO_3$ | 3 |
| $-NH-CH_2CH_2-\text{(2,5-dimethylphenyl)}$ | $-CH_3$ | $-CH_3$ | $-CH_3$ | $-CH_3$ | $Cl^-$ | 3 |
| $-NHCH_2CH_2-\text{(6-methylpyridin-2-yl)}$ | $-CH_3$ | H | H | $CH_3$ | $CF_3SO_3$ | 2 |

TABLE IV-continued

| R | R¹ | R² | R³ | R⁴ | Anion or Salt | n |
|---|---|---|---|---|---|---|
| 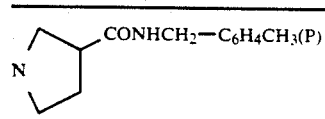 (N-pyrrolidinyl with CONHCH₂—C₆H₄CH₃(P)) | —CH₃ | —CH₃ | H | CH₃ | Cl⁻ | 2 |
| 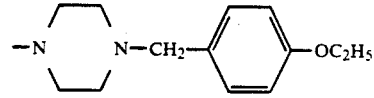 (piperazinyl-N-CH₂-C₆H₄-OC₂H₅) | —CH₂C₆H₅ | H | H | —CH₂C₆H₅ | Cl⁻ | 3 |
| 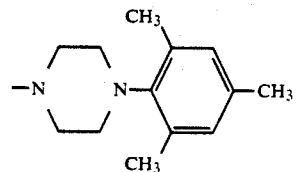 (piperazinyl with 2,4,6-trimethylphenyl) | —CH₃ | H | H | CH₃ | CF₃SO₃⁻ | 2 |
| 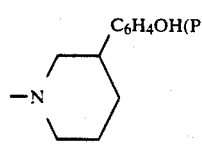 (piperidinyl with C₆H₄OH(P)) | —CH(CH₃)₂ | H | H | —CH(CH₃)₂ | CF₃SO₃⁻ | 2 |
| 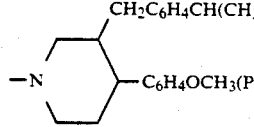 (piperidinyl with CH₂C₆H₄CH(CH₃)₂(P) and C₆H₄OCH₃(P)) | —CH₃ | H | H | —CH₃ | Cl⁻ | 3 |
| 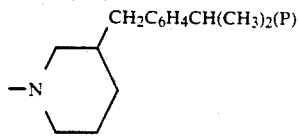 (piperidinyl with CH₂C₆H₄CH(CH₃)₂(P)) | —CH₃ | —C₃H₇(n) | —C₃H₇(n) | —CH₃ | Cl⁻ | 3 |

EXAMPLE XIV

The following salts are prepared by intimately mixing the imidazole in ethanolic hydrogen chloride, letting the mixture stand at ambient temperature to allow the crystals of the salt to form and then recovering by filtration.

Phenyl 6-[1-methylimidazol-2-yl]thio-5-oxo-hexanoate·hydrochloride;

Benzyl 6-[1-ethylimidazol-2-yl]thio-5-oxo-hexanoate·hydrochloride;

N-2-phenylethyl 6[1-methylimidazol-2-yl]thio-5-oxo-hexanamide·hydrochloride.

EXAMPLE XV

Parenteral Composition

One liter of a parenteral composition comprising one of the foregoing compounds may be prepared from the following formulation:

|  | Grams |
|---|---|
| Imidazolium salt | 5.0 |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |

-continued

|  | Grams |
|---|---|
| Water, USP | q.s. to 1 liter |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water, and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

EXAMPLE XVI

Oral Composition 5000 compressed tablets, each containing as active ingredient 100 milligrams of one of the foregoing compounds, may be prepared from the following formulation:

|  | Grams |
|---|---|
| Imidazolium salt | 500 |
| Starch | 700 |

| | Grams |
|---|---|
| Dibasic calcium phosphate hydrous | 5000 |
| Calcium stearate | 25 |

The ingredients are finely powdered, mixed well, and then granulated with 10 percent starch paste. The granulation is dried and compressed into tablets using starch as a disintegrant and calcium stearate as lubricant.

Preparation of the Starting Materials

A. 2-Mercaptoimidazole

The 2-mercaptoimidazoles may be obtained by a reaction between an appropriate acyloin and mono-substituted thiourea according to the following equation:

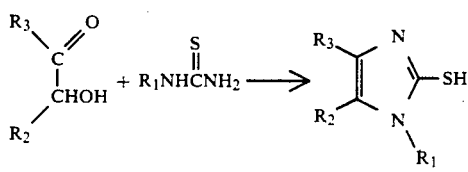

The reaction may be carried out by fusing the reactants or by refluxing the components in hexanol-1 as more fully described by Nuhn, P. et. al., J. fur praktische Chemie, 312, 90 (1970) for the fusion method and by Kjellin, G. et. al., Acta Chemica Scandinavica, 23, 2879 (1969) for the method where the α-hydroxyketones and N-alkylthioureas are refluxed in 1-hexanol with a water separator. When R, is benzyl, i.e., a phenyl-substituted alkyl, the preferred method is refluxing the α-hydroxyketone with N-benzylthiourea in hexanol with a water separator. When $R_2$ and $R_3$ are cycloalkyl, the method employed also is by refluxing the α-hydroxyketone, namely

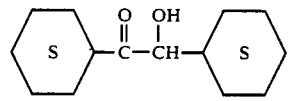

with the desired N-alkylthiourea or N-benzylthiourea. The teachings of the foregoing articles on the preparation of the starting 2-mercaptoimidazoles are incorporated by reference.

The acyloins may be prepared in any manner within the knowledge of those skilled in the art.

B. Acylmethyl halide (Compound B)

The starting acylmethyl halide for preparing the side chain and represented by the formula

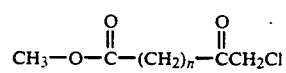

may be obtained from the mono-ester mono-acid chloride of dibasic acids

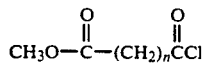

by generating diazomethane in a manner described in Fieser et al., "Reagent for Organic Synthesis" Vol I, p 191-2, John Wiley & Sons, Inc, 1967 (and which is incorporated by reference) and the acid chloride in diethyl ether added dropwise to the freshly generated solution of diazomethane and the reaction mixture stirred at dry ice temperature. After completion of the addition the mixture is allowed to warm to 0° C. The diazomethane is removed under aspirator vacuum, and hydrogen chloride in ethanol added dropwise thereto and stirred first at ice bath temperature, then at room temperature and the resulting mixture then concentrated to dryness to obtain the chloro alkanoate starting material.

What is claimed is:

1. A composition suitable for thrombolytic therapy in unit dosage form comprising (a) a plasminogen activator selected from the groups consisting of tPA in an amount of about 58 million I.U. and streptokinase in an amount of 1.5 million I.U. and (b) an imidazole compound in an amount of from 100 mg to 10 grams in a pharmaceutically acceptable carrier, wherein said imidazole compound is selected from the group consisting (A) an imidazole having the formula:

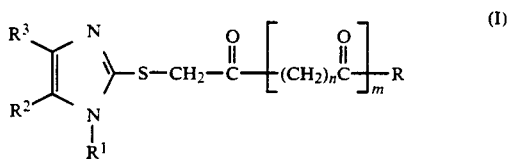

or its acid addition salt, and (B) an imidazolium salt having the formula:

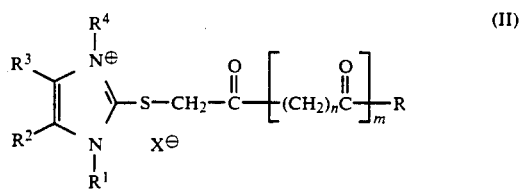

wherein in the above formulas
R is OR' or NR"R'";
wherein:
R' is hydrogen, lower alkyl, lower alkanoyl, phenyl, or substituted phenyl having from 1 to 3 substituents selected from hydroxy, alkoxy, alkyl, and nitro and from 1 to 5 substituents when the substituent is halo:
R" is hydrogen, lower alkoxy,

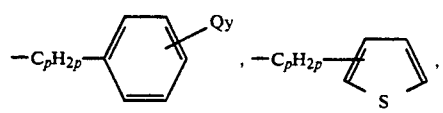

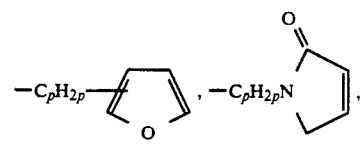

-continued

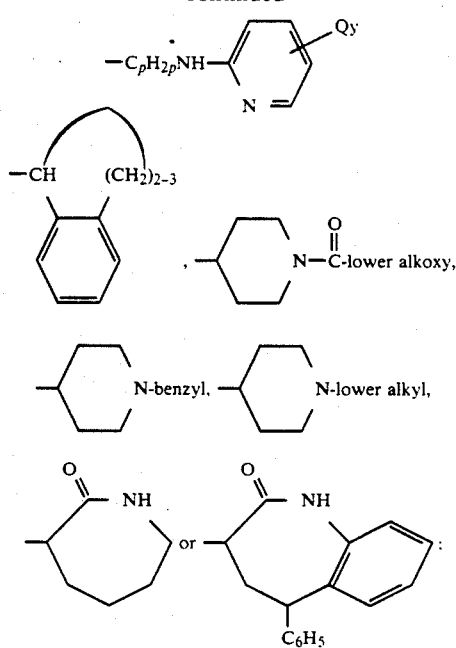

R''' is hydrogen or lower alkyl; or
R'' and R''' together with N is

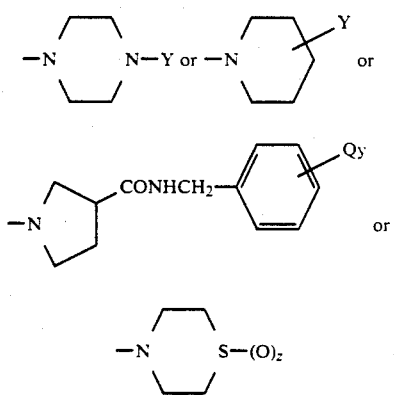

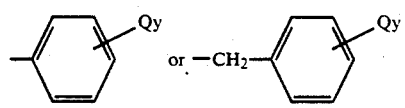

wherein in the foregoing and subsequent formulas Q is independently hydroxy, lower alkoxy lower
alkyl, halo and nitro
Y is lower alkyl,

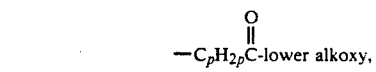

p is 1 to 4
y is 0 to 4, and
z is 0 to 2
$R^1$ is lower alkyl, benzyl;
$R^2$ is hydrogen, lower alkyl, or cycloalkyl;
$R^3$ is hydrogen, lower alkyl, or cycloalkyl;
$R^4$ is lower alkyl, benzyl;
$R^2$ and $R^3$ taken together form an alkylene chain of 3 to 10 carbon atoms;
X is an anion of a pharmaceutically acceptable salt;

m is 0 or 1; and
n is from 0 to 3;
  provided that when n is 0, m is 0.
2. A composition according to claim 1 wherein the plasminogen activator is tPA.
3. A composition according to claim 1 wherein the plasminogen activator is streptokinase.
4. A method for inhibiting hard clot formation or supplementing fibrinolytic therapy which comprises administering to a patient in need of such treatment (a) from 1 µg to 100 µg/kg/min. for a day of an imidazole compound together with (b) an antithrombotic agent; wherein said imidazole compound is selected from the group consisting of
  (A) an imidazole having the formula;

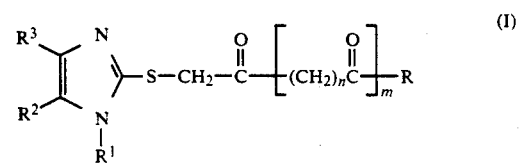

or its acid addition salt, and
(B) an imidazolium salt having the formula;

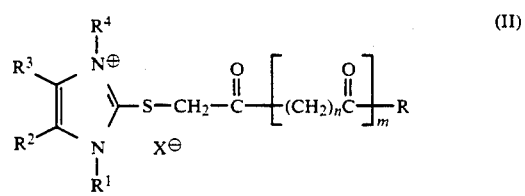

wherein in the above formulas
R is OR' or NR''R''';
wherein:
  R' is hydrogen, lower alkyl, lower alkanoyl, phenyl, or substituted phenyl having from 1 to 3 substituents selected from hydroxy, alkoxy, alkyl, and nitro and from 1 to 5 substituents when the substituent is halo;
  R'' is hydrogen, lower alkyl,

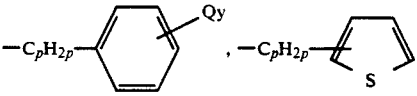

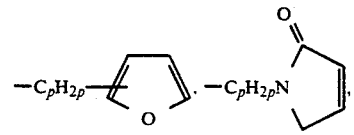

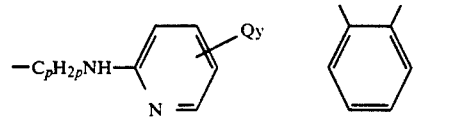

-continued

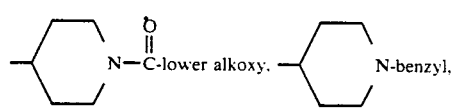

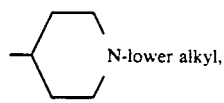

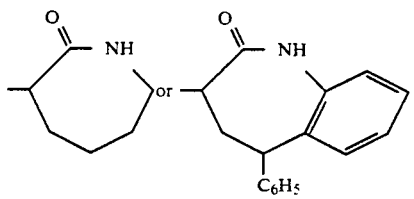

R''' is hydrogen or lower alkyl; or
R'' and R''' together with N is

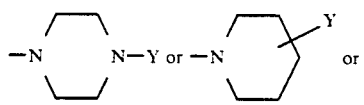

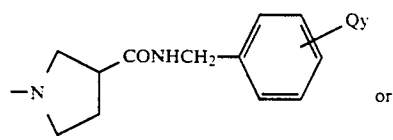

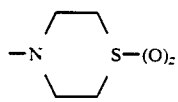

wherein in the foregoing and subsequent formulas

Q is independently hydroxy, lower alkoxy lower alkyl, halo and nitro

Y is lower alkyl,

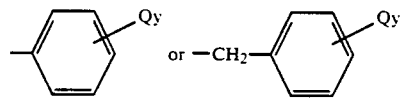

p is 1 to 4
y is 0 to 4, and
z is 0 to 2
$R^1$ is lower alkyl, benzyl;
$R^2$ is hydrogen, lower alkyl, or cycloalkyl;
$R^3$ is hydrogen, lower alkyl, or cycloalkyl;
$R^4$ is lower alkyl, benzyl;
$R^2$ and $R^3$ taken together form an alkylene chain of 3 to 10 carbon atoms;
X is an anion of a pharmaceutically acceptable salt;
m is 0 to 1; and
n is from 0 to 3;
provided that when n is 0, m is 0; and
wherein said antithrombotic agent is (i) a plasminogen activator; (ii) a platelet aggregation inhibitor or (iii) an anticoagulant.

5. A method according to claim 4 wherein the antithrombotic agent is a plasminogen activator selected from the group consisting of tissue plasminogen activator (tPA), prourokinase (single chain urokinase), urokinase (dual chain urokinase), streptokinase and eminase, and the plasminogen activator is used in the dose range of about 500 to 10,000 I.U./kg/min. for from about 30 to 180 minutes.

6. A method according to claim 4 wherein the antithrombotic agent is a platelet aggregation inhibitor selected from the group consisting of aspirin and dipyridamole; and a semi-synthetic peptide available as "Echistatin," and a semi-synthetic peptide available as "Bitistatin" wherein the platelet aggregation inhibitor (a) if aspirin, is administered at a dose of 25-325 mg once or twice a day; if dipyridamole, is administered at a dose of 25 to 100 milligrams four times a day, and (b) if a semi-synthetic peptide available as "Echistatin" or as "Bitistatin", is administered in a dose range of 0.1 to 1 nanomole/kg/min. for from 30 to 180 minutes.

7. A method according to claim 4 wherein the antithrombotic agent is an anticoagulant selected from the group consisting of heparin and of coumarin drugs wherein the anticoagulant (a) if heparin, is administered at doses of 4000 to 8000 units per four hours, and (b) if coumarin, drugs is administered orally at doses of 10 to 15 mg/kg/day.

* * * * *